United States Patent [19]

Warshawsky et al.

[11] 4,317,887
[45] Mar. 2, 1982

[54] METAL COMPLEXING POLYMERS

[75] Inventors: Abraham Warshawsky, Rehovot; Rami Kalir, Netanya; Abraham Patchornik, Nes Ziona, all of Israel

[73] Assignee: Yeda Research and Development Co. Ltd., Rehovot, Israel

[21] Appl. No.: 65,751

[22] Filed: Aug. 10, 1979

Related U.S. Application Data

[63] Continuation-in-part of Ser. No. 817,806, Jul. 21, 1977, abandoned.

[30] Foreign Application Priority Data

| Jul. 25, 1976 [IL] | Israel | 50119 |
|---|---|---|
| Jul. 21, 1977 [CA] | Canada | 283294 |
| Jul. 22, 1977 [DE] | Fed. Rep. of Germany | 2733251 |
| Oct. 4, 1978 [ZA] | South Africa | 77/4290 |

[51] Int. Cl.$^3$ .......................................... B01J 45/00
[52] U.S. Cl. .................................... 521/38; 521/25; 75/101 BE
[58] Field of Search ................................... 521/38, 25

[56] References Cited

U.S. PATENT DOCUMENTS

| 4,012,362 | 3/1977 | Peiff et al. | 521/25 |
|---|---|---|---|
| 4,207,399 | 6/1980 | Kambaro | 525/375 |
| 4,220,726 | 9/1980 | Warshawsky | 75/101 BE |

FOREIGN PATENT DOCUMENTS

| 54-139989 | 10/1979 | Japan | 521/31 |
|---|---|---|---|
| 483405 | 11/1973 | U.S.S.R. | 521/25 |

*Primary Examiner*—William F. Hamrock
*Assistant Examiner*—Peter F. Kulkosky
*Attorney, Agent, or Firm*—Browdy and Neimark

[57] ABSTRACT

Novel polyfunctional compounds and polymers are disclosed of the general formula

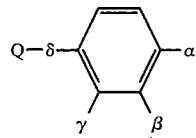

wherein Q designates -X' or -X-ε-R;
where X' designates

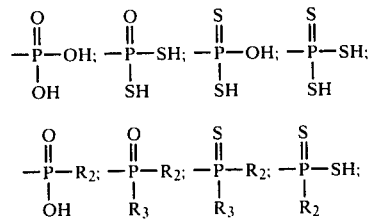

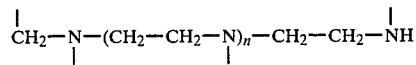

$-NH(-CH_2-CH-NH)_n-R_4$; or $-O(-CH_2CHO)_nR_4$;
$\quad\quad\quad\quad |$
$\quad\quad\quad R_3 \quad\quad\quad\quad\quad\quad\quad\quad\quad\quad\quad R_3$ where
α is —OH, or —SH;
β is —OH, —SH, —NH$_2$, —NO$_2$, —CO—R$_2$, —R$_2$C=N—OH, —COOH, -hal, alkyl, aryl, or aralkyl; halogen being chlorine or bromine;
γ is a non-interfering substituent;
where β and γ may form together a hydrocarbyl ring system;
where δ is —(CH$_2$)$_n$— or —SO$_2$—;
where X is —O—, —S—, —NH—, —N$^+$R$_2$R$_3$Cl$^-$ or —P—;
where
ε is —(CH$_2$)$_n$—, —SO$_2$—, —NH— or —CH$_2$(O-CH$_2$—CH$_2$)$_n$—;

$\quad |\quad\quad\quad\quad\quad\quad\quad\quad\quad\quad\quad\quad\quad\quad\quad\quad |$
$CH_2-N-(CH_2-CH_2-N)_n-CH_2-CH_2-NH$
$\quad\quad |\quad\quad\quad\quad\quad\quad\quad |$ wherein the upwardly directed bonds are connected to the R polymer molecule and the downwardly directed bonds are connected to δ groups;
n is an integer of from 1 to 15 or zero;
R is a polymeric backbone, alkyl or aralkyl; and
R$_2$, R$_3$ and R$_4$ which may be identical or different, each designates hydrogen, alkyl, aryl or aralkyl. These compounds are useful as ion-exchange agents, extractants, biocides, flameproofing agents, fire retardants, metal polishing agents and rust inhibitors. Metals may be selectively extracted from solution thereof by means of these compounds and polymers.

10 Claims, No Drawings

METAL COMPLEXING POLYMERS

CROSS-REFERENCE TO RELATED APPLICATIONS

The present application is a continuation-in-part of U.S. application Ser. No. 817,806 filed July 21, 1977 now abandoned, the entire contents of which are hereby incorporated by reference.

SUMMARY OF THE INVENTION

The present invention relates to novel polyfunctional compounds and polymers of the general formula

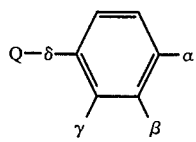

wherein Q designates -X' or -X-$\epsilon$-R;
where X' designates

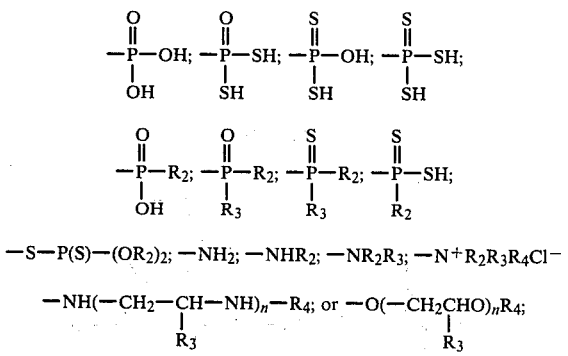

$-S-P(S)-(OR_2)_2$; $-NH_2$; $-NHR_2$; $-NR_2R_3$; $-N^+R_2R_3R_4Cl^-$ $-NH(-CH_2-\underset{R_3}{CH}-NH)_n-R_4$; or $-O(-CH_2\underset{R_3}{CHO})_nR_4$;

where
$\alpha$ is $-OH$, or $-SH$;
$\beta$ is $-OH$, $-SH$, $-NH_2$, $-NO_2$, $-CO-R_2$, $-R_2C=N-OH$, $-COOH$, -hal, alkyl, aryl, or aralkyl; halogen being chlorine or bromine;
$\gamma$ is a noninterfering substituent;
where $\beta$ and $\gamma$ may form together a hydrocarbyl ring system;
where $\delta$ is $-(CH_2)_n-$ or $-SO_2-$;
where X is $-O-$, $-S-$, $-NH-N^+R_2R_3Cl-$ or $-P-$;
where
$\epsilon$ is $-(CH_2)_n-$, $-SO_2-$, $-NH-$ or $-CH_2(O-CH_2-CH_2)_n$;
n is an integer of from 1 to 15 or zero;
R is a polymeric backbone, alkyl or aralkyl; and
$R_2$, $R_3$ and $R_4$ which may be identical or different, each designates hydrogen, alkyl, aryl or aralkyl; and to a process for the production of the above compounds.

In the context of this application the term "polymeric backbone" designates a suitable polystyrene or polystyrene copolymer, a polyacrylamide, or a polysaccharide.

Alternatively, the -X-$\epsilon$- group may be

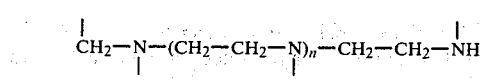

wherein the upwardly directed bonds are connected to the R polymer molecule and the downwardly directed bonds are connected to $\delta$ groups.

For the preferred compounds of the present invention, in the above formula:
$\alpha$ is $-OH$ or SH;
$\beta$ is $-OH$, $-SH$, $-NH_2$, $-NO_2$, $-COR_1$,

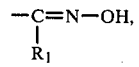

or $-COOH$, $R_1$ being hydrogen, alkyl or aralkyl;
$\gamma$ is hydrogen, or $\beta$ and $\gamma$ are linked together to form a second aromatic ring which forms a quinoline ring system in combination with the original ring;
$\delta$ is $-CH_2-$ or $-SO_2-$; and
Q is $-NHR_2$, $-NR_2R_3$, $-N^+R_2R_3R_4Cl^-$,

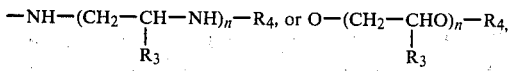

wherein
n is zero or an integer of 1 to 5, and wherein R, $R_2$, $R_3$, $R_4$, X and $\epsilon$ are as defined hereinabove.

The compounds of the present invention can be produced by various processes, e.g.:

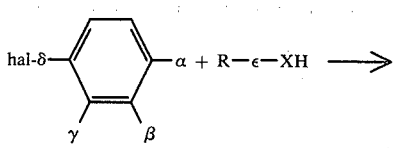

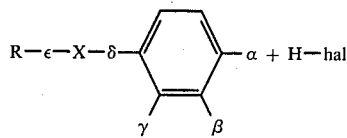

The following examples are by way of illustration only. In those where functional groups are attached to a polymer backbone, only one representative functional moiety is shown. Novel compounds according to the present invention are useful ion-exchange agents, extractants, biocides, flameproofing agents, fire retardants, metal polishing agents, and rust inhibitors.

Some of the compounds represented by the formula

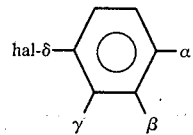

are described in the literature, (1) J. Mathieu and J. Weill-Raynal in "Formation of C-C Bonds", Georg Thieme Publishers Stuttgart (1973), and (2) K. Leroy Nelson in "Friedel Crafts and Related Reactions, Sulfonation", G. A. Olah Edit. Vol. 3, Part 2, p. 1355. Of particular use in this invention are compounds according to the above mentioned formula which contain metal complexing groups. Some examples of these wherein $R_2$ and $R_3$ are as defined above are:

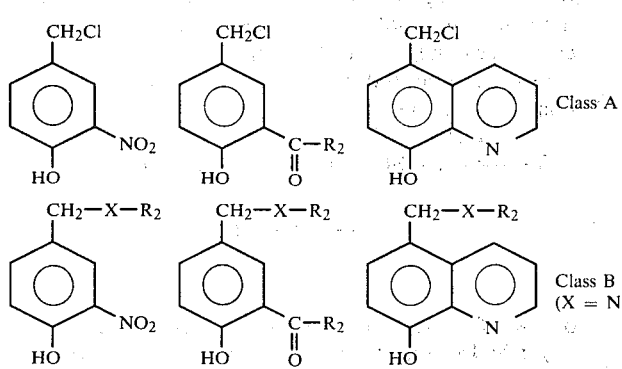

Class A

Class B
(X = NR₃ or O)

The chloromethyl compounds (described herein as Class A compounds) may be reacted with nucleophilic reagents according to Route A, mentioned above to yield liquids or polymers useful as ion exchangers, as described in the examples. (Only one typical group attached to a polymer is shown).

DESCRIPTION OF PREFERRED EMBODIMENTS

Reaction of Class A Compounds with Polyamines

EXAMPLE 1

Production

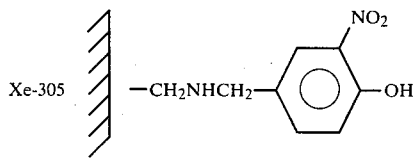

10 g of polymethylamino styrene (Xe-305*, 9.1% N) was reacted with 12 g of 2-nitro-4-chloromethyl phenol at 65° for 24 hours in 100 ml CHCl₃ to yield 22 g monosubstituted product containing 8.4% nitrogen.

*Amberlytes-Xe-305; XAD-2 designating the backbones are macroporous polystyrenes produced by Rohm and Haas, U.S.A. The solid line stands for the backbone chain of the polymer. Polymethylaminostyrene was produced by the method of G. Rossey and A. Patchornik, Israel Patent Appl. No. 52121.

EXAMPLE 2

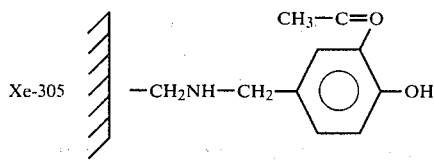

10 g of polymethylamino styrene (Xe-305, 9% N) was reacted with 12 g of 2-acetyl-4-chloromethyl phenol in 100 ml CHCl₃ at 65° C. for 24 hours to yield 23 g of monosubstituted product containing 4.9% N. The oxime was prepared by reflux with hydroxylamine hydrochloride (10 g) in methanol (50 ml). Product: 23 g, 8.2% N.

EXAMPLE 3

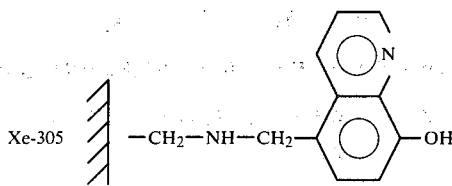

10 g of polymethylaminostyrene (Xe-305; 9% N) were reacted with 15 g of 5-chloromethyl-8-hydroxyquinoline in CHCl₃ at 64° C. for 24 hours. The product 24 g, contains 4.2% N.

EXAMPLE 4

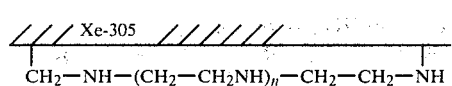

$CH_2-NH-(CH_2-CH_2NH)_n-CH_2-CH_2-NH$

Chloromethylpolystyrene (Xe-305 type) containing 20% chlorine was reacted with polyethyleneimine of various molecular weights (n=1–20) in chloroform at 64° C. or in dioxane/H₂O mixture at 100° C. for 24 hours to yield quantitative conversions of chlorine residues into amino residues (for each chlorine atom, one ethylene unit was introduced).

4(a)

In a typical experiment 10 g of Xe-305/CH₂Cl was reacted with 5 g polyethyleneimine (n=8) of average molecular weight 400 in 50 ml CHCl₃ at 64° C. to yield 12 g product containing 1.5% chlorine and 7.2% N.

4(b)

10 g of Xe-305/CH₂Cl were reacted with 5 g polyethyleneimine (n=23) of average molecular weight 1000 to yield 12.5 g of product containing 0.7% chlorine and 6.1% N.

EXAMPLE 5

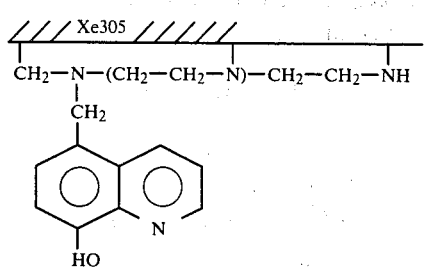

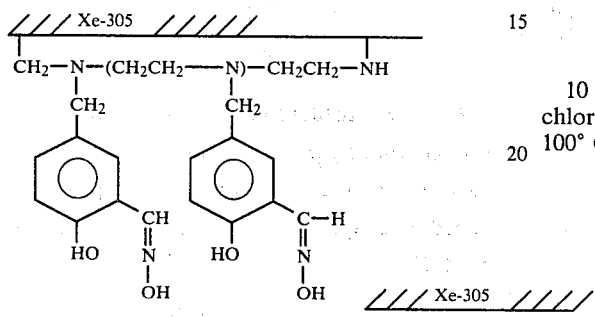

Class A compounds were reacted with many of the polymers described in Example 4.

5(a)

10 g of the polymer of Ex. 4(a) were reacted with 12 qr of 2-formyl-4-chloromethylsalicyl-aldehyde in 50 ml CHCl₃ at 64° C. for 20 hours to yield 22 g of product containing 4.5% N, which was further converted to its oxime by reaction with 15 g hydroxylamine hydrochloride in 75 ml methanol. The yield; 22 g; contains 8.2% N.

5(b)

10 g of the polymer of Example 4(b) were reacted with 15 g of 5-chloromethyl-8-hydroxy-quinoline in 50 ml CHCl₃ at 64° C. for 20 hours to yield 23 g of a product containing 3.9% N.

Reaction of Class A compounds with Polyols

Polyalcohols were prepared by reacting chloromethylpolystyrene with large excess of polyoxyalkylene in dioxane at 100° C. as shown in Examples 6-8.

EXAMPLE 6

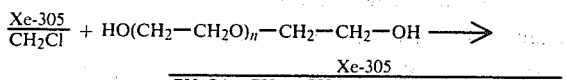

6(a)

15 g of Xe-305/CH₂Cl containing 20% chlorine was reacted with 50 g diethylene glycol in 100 ml dioxane at 100° C. for 20 hours, 22 g product.

6(b)

15 g of Xe-305/CH₂Cl was reacted with 100 g triethylene glycol in 100 ml dioxane for 24 hours, product 26 g.

EXAMPLE 7

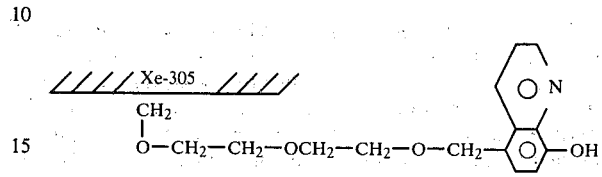

10 g of polymer 6(a) were reacted with 12 g of 5-chloromethyl-8-hydroxy-quinoline in 50 ml dioxane at 100° C. to yield 21.3 g product containing 3.6% N.

EXAMPLE 8

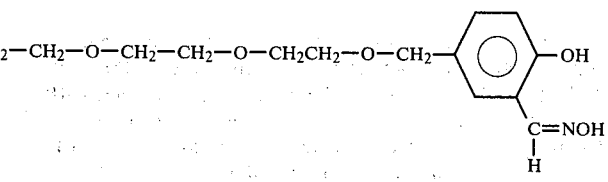

10 gr of polymer 6(b) were reacted with 12 g of 2-formyl-4-chloromethylphenol at 100° C. in 50 ml dioxane the product, 19 g, was converted to the dioxime by adding 10 g hydroxylamine hydrochloride and further reaction for five hours. Product: 19 g; 3.5% N.

EXAMPLE 9

Binding to polyacrylamide backbone

Polyacrylamide beads, also described as Bio-gels, are provided by Biorad Laboratories, or by other producers, may be modified into polymers containing amino acids residues, as described by Innman and Dintzis (*Biochemistry*, 8, 4074 (1969)).

A polyacrilamide gel of the P-6 type, known to exclude compounds of molecular weight higher than 6000 was modified into its ethylamine derivative having the following formula:

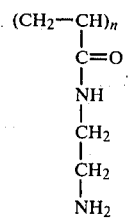

10 g of this polymer containing 1.5 mmole primary amine units were swollen in dioxane (100 ml) for 24 hours and reacted with 10 g of chloromethylsalicylaldehyde, or with 10 g of 5-chloromethyl-8-hydroxyquinoline, to yield 15 g or 18 g respectively of products.

EXAMPLE 10

Producing of Extraction Agents

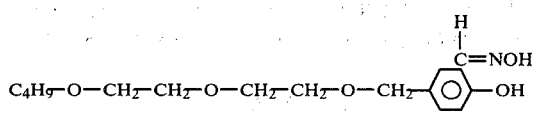

17 g of 2-formyl-4-chloromethylphenol were reacted with 100 ml diethyleneglycol monobutyl ether at 120°–160° C. for 48 hours, the product was washed with water and turned into the oxime by reaction with 20 g hydroxylamine in 100 ml methanol at reflux for 5 hours in the presence of (10 ml) triethylamine work up yielded 30 g product as oil cont. 3.8% N.

EXAMPLE 11

Production of

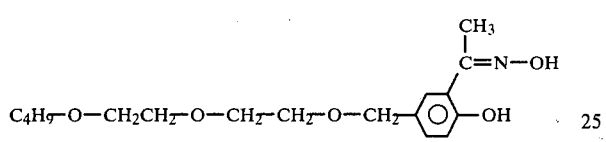

19 g of 2-acetyl-4-chloromethylphenol were reacted with 100 ml diethyleneglycolmonobutylether at 120°–160° C. for 48 hours, the product was washed with water and turned into the oxime by reaction with 20 g hydroxylamine hydrochloride in 100 ml methanol in the presence of 10 ml triethylamine at reflux temperature for 5 hours. Usual work up yielded 32 g product cont. 3.6% N.

EXAMPLE 12

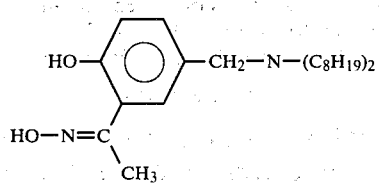

19 g of 2-acetyl-4-chloromethylphenol were reacted with 34 g di-n-octylamine in 100 ml chloroform at room temp. for 20 hours; the solution was washed with water, dried, and excess solvent removed; the remaining oil was reacted with 20 g hydroxylamine hydrochloride, 10 g, triethylamine in 100 ml methanol reflux for 5 hours; the product was worked up to yield 35 g of oil. Cont. 2.6% N.

EXAMPLE 13

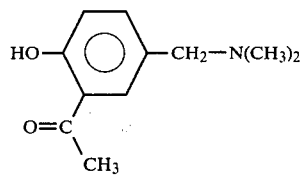

19 g of 2-acetyl-4-chloromethylphenol were reacted with excess methylamine in methanol (50 ml of 20% solution) at 5°–10° C. for 2 hours and left at 100 temperature for 20 hours, the product, methyl-di-aryl type tertiary amine, could be further converted to the oxime by the procedure described in examples 10–12, or could be reacted in other ways, as will be described.

EXAMPLE 14

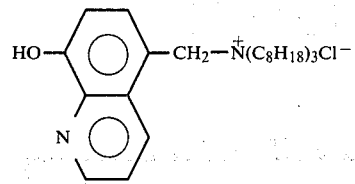

23 g of 5-chloromethyl-8-hydroxyquinoline were reacted with 7.2 g trioctylamine in 100 ml methanol at room temperature for 20 hours. The product was obtained by evaporation of the solvent. 29 gr containing 5.2% N.

EXAMPLE 15

Conversion of Class A Compounds to Class B Compounds

The chloromethyl derivatives described as Class A, when left with equimolar amounts of ammonia, alkyl amines, or sodium hydroxide in methanol or any suitable solvent for a period between several hours to several days at ambient conditions will yield Class B Compounds which may be isolated by evaporating the amine or by removing the amine by means of an acidic solution, or by passing it through a suitable sulphonic acid type ion exchanger. This conversion is described in Examples 12–14.

EXAMPLE 16

Bonding of Class B Compounds to Polymer Backbones

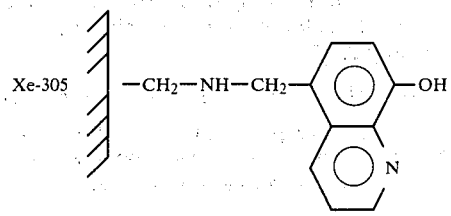

20 g of chloromethylpolystyrene type Xe-305 containing 20% Cl was reacted in 100 ml dioxane at reflux, with 40 g of the amine derivate described above in example 14 for 20 hours to yield 32 g of product containing 2.2% N.

EXAMPLE 17

Production of $$\text{Xe-305} - \text{CH}_2 - \overset{+}{\underset{\underset{Cl^-}{CH_3}}{\overset{CH_3}{N}}} - CH_2 - \underset{\underset{CH_3}{C=N-OH}}{\bigcirc} - OH$$

20 g of chloromethylpolystyrene, type Xe-305, containing 20% Cl, was reacted in 100 ml dioxane at reflux for 24 hours with 38 gr of the amine described in Example 13. The product 30 g was further converted to the oxime by reaction with 15 g hydroxylamine hydrochloride in the presence of 10 ml triethylamine.

Biological active agents with metal chelating centers—by reaction of Class A & Class B Compounds with phosphoric and thiophosphoric acids derivatives.

EXAMPLE 18

Reactions with phosphorous oxychloride $$O=PCl_3 + HOCH_2-\underset{NO_2}{\bigcirc}-OH \longrightarrow$$

$$\left( O=P \left[ -O-CH_2-\underset{NO_2}{\bigcirc}-OH \right]_3 \right)$$

3-Nitro-4-hydroxybenzylalcohol, 3-formyl-4-hydroxy benzylalcohol, and 5-methylol-8-hydroxy quinoline could be reacted with POCl₃ at 5°–10° C. to produce the corresponding triesters: The alcohol (0.3 mole) in 100 ml benzene was added to 0.1 mole POCl₃ in 100 ml benzene at 0°–10° C. during 2 hours. The mixture was left at room temperature for 20 hours, and the product washed with water, dried, and solvent removed.

EXAMPLE 19

Reaction with Thiophosphoryl Chlorides

The reagent β is prepared according to the following scheme:

$$HO-\underset{O_2N}{\bigcirc}-CH_2OH \xrightarrow[(2) Cl_2]{(1) P_2S_5}$$

-continued $$\left( HO-\underset{O_2N}{\bigcirc}-CH_2O \right)_2 PSCl$$

3-Nitro-4-hydroxybenzyl alcohol (0.1 mole) is mixed together with phosphorous pentasulfide (0.05 mole) at 100° C. for 20 hours, and the product is distilled off under vacuum (1 torr) and could be reacted further with various alcohols.

In the same manner 3-formyl-4-hydroxybenzyl alcohol and 5-hydroxymethylol-8-hydroxy quinoline could be reacted.

EXAMPLE 20

Production of dithiophosphates $$(CH_3O)_2P(S)SCH_2-\underset{\bigcirc_N}{\bigcirc}-OH$$

0.1 Mole of dimethyldithiophosphate sodium salt in 200 ml acetone is added dropwise to 0.1 mole 5-chloromethyl-8-hydroxyquinoline in 100 ml acetone at room temperature. The reaction mixture is refluxed for three hours, and the salt is removed by filtration. The solvent is removed by distillation to yield the crude product (0.1 mole).

In a similar way dimethyltiophosphate could be reacted with 4-chloromethyl-2-nitrophenol, 4-chloromethyl-salicylaldehyde, 4-chloromethyl-2-acetylphenol.

EXAMPLE 21

Production of Organophosphorous Compounds $$C_6H_5-P(S)-CH_2-\underset{}{\overset{NO_2}{\bigcirc}}-OH$$

Phenylphosphorodithioic chloride (0.1 mole) in chlorobenzene (100 ml) is reacted with 0.1 mole 4-hydroxymethyl-2-nitrophenol at 100° C. for 24 hours. The solvent is distilled of: Yield—40%.

EXAMPLE 22

Chlorosulphonation of Polystyrene 20 g of polystyrene (XE-305) were swollen in 100 ml of ethanol-free chloroform for 0.5 hour. 250 ml of chlorosulphonic acid dissolved in 50 ml CHCl₃ was added dropwise at 0°–4° C. during 1 hour. The polymer was left to stand overnight while the temperature increased to ambient temperature. The product was filtered and washed with chloroform, dry ether, and dried. 14.32% S and 14.10% Cl.

EXAMPLE 23

Reactions of Chlorosulphonyl Polystyrene with various Nucleophiles a.

5 g of chlorosulphonyl polystyrene (Ex. 22) were swollen in 50 ml chloroform. Then 5 g of tetraethylene pentamine were added, and the reaction proceeded at room temperature for 20 hours. The polymer was filtered and washed with chloroform. 8.1 g containing 10.7% N.

b.

5 g of chlorosulphonyl polystyrene (Ex. 22) were swollen in 100 ml chloroform, and then 5 g of 5-aminomethyl-8-hydroxyquinoline was added in 50 ml dioxane. The reaction proceeded at room temperature for 20 hours. The polymer was filtered and washed with chloroform, dioxane, water and methanol, and then dried. 7.2 g containing 4.2% N.

EXAMPLE 24

Reactions Between Aminated Polymers and 4-Chlorosulphonyl-2-Acetylphenol 10 g of polymethylaminostyrene (XE-305: 9% N) as described in Example 1 was swollen in 100 ml ethanol free chloroform, then 10 g of 4-chlorosulphonyl-2-acetyl phenol was added at 0°–4° C. in portions. The reaction mixture was allowed to warm up gradually. After 20 hours the polymer was filtered and washed with chloroform, methanol, and dried. 14.2 g containing 7.5% S.

Similarly, polymers of Example 4 containing polyethylenamine were reacted to yield product of 9.2% S.

EXAMPLE 25

Reactions Between Animated Polymers and 5-Chlorosulphonyl-8-Hydroxyquinoline 5 chlorosulphonyl-8-hydroxy quinoline was prepared from the corresponding acid and thionyl chloride at reflux temperature. 5 g of this compound were added at 0°–4° C. to 5 g polymethylamino styrene (Ex. 1) as 5 g polyethylanimine (Ex. 4(a)) was swollen in 30 ml CHCl₃. After 20 hours the polymer was filtered and washed with chloroform and methanol and dried to yield 7.9 g and 8.4 g products respectively.

EXAMPLE 26

Metal Complexing Properties of Polymers

All the polymers described were tested for their metal binding capacity under various conditions such as: metal ion concentration, pH, varying anion types and concentration. Also various eluting conditions were investigated. In all experiments 10 g samples of polymer were contacted for 24 hours with 100 ml of 0.1 M solutions of the metal salt adjusted to the right pH. The metal capacity was determined by analyzing solution before and after contact with polymer, and also by direct determination of metal ion concentration in an eluting solution, such as 3 N $H_2SO_4$. Some typical values for several polymers are given in the next table.

| METAL CAPACITY (mmole/g) FOR SEVERAL POLYMERS | | | | | | |
|---|---|---|---|---|---|---|
| | | metal | | | | |
| Polymer type | Ex. no. | $Fe^{3+}$ | $Cu^{2+}$ | $Co^{2+}$ | $Zn^{2+}$ | $Ni^{2+}$ |
| polymethyl amino | — | 0.8 | 0.05 | 0.3 | 0.8 | 0.7 |

*-continued*

| METAL CAPACITY (mmole/g) FOR SEVERAL POLYMERS | | | | | | |
|---|---|---|---|---|---|---|
| | | metal | | | | |
| Polymer type | Ex. no. | $Fe^{3+}$ | $Cu^{2+}$ | $Co^{2+}$ | $Zn^{2+}$ | $Ni^{2+}$ |
| styrene hydroxyquinoline | 3 | 0.77 | 0.79 | 0.08 | 0.6 | 0.7 |
| ethyleneimine | 4/a | 1.1 | 0.1 | 0.7 | 0.6 | 0.8 |

Some of the separation potentialities are obvious. For example, 50 ppm of zinc ions in 20 gpl cobalt sulphate were eliminated successfully by treating said solutions with polymer of Ex. 3, producing an outcoming solution of 0.16 ppm $Zn^{2+}$ ions. In another application polymer of Ex. 4(b) was used to separate $Fe^{3+}$ ions from $Cu^{2+}$ ions at pH 2. In another application polymer of Ex. 3 was used to coextract $Fe^{3+}$ and $Cu^{2+}$ ions from pH 2 sulphate solutions, leaving behind other base metals. Other applications are also possible.

EXAMPLE 27

Liquid-Liquid Extraction

Reagents as described in Examples 10 to 14 when diluted in inert diluents may be used to extract metal values in said solvents in a selective or a general manner, separating a group of ions from another group, or extracting a single ion from a group. The hydroxyoximes described in Examples 10, 11 and 12 are designed to selectively extract copper from iron and other base metals. Whereas the reagent described in Example 14 is a general transition, metal extractant. Reagents in Examples 10, 11, and 12 extract copper from acidic solutions of pH 2–4 and release the ions upon contact with 0.5 N $H_2SO_4$.

It will be obvious to those skilled in the art that various changes may be made without departing from the scope of the invention and the invention is not to be considered limited to what is described in the specification.

What is claimed is:

1. A metal complexing polymer of the general formula

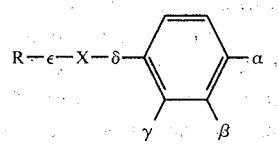

wherein

α is —OH or —SH;

β is —OH, —SH, $NH_2$, —$NO_2$, —$COR_1$,

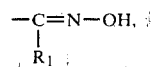

or —COOH, $R_1$ being hydrogen, alkyl or aralkyl;

γ is hydrogen, or β and γ are linked together to form a second aromatic ring which forms a quinoline ring system in combination with the original ring;

δ is —$CH_2$— or —$SO_2$—;

R is a polymer backbone comprising polyacrylamide, polystyrene, or divinylbenzene cross-linked polystyrene;

ε is —$(CH_2)_n$— or —$CH_2(OCH_2—CH_2)_n$—;

X is —NH—, —N⁺R₂R₃Cl⁻— or —O—; or
-X-ε- is $$\overset{|}{CH_2}-\overset{}{N}-(CH_2-CH_2-\overset{}{N})_n-CH_2-CH_2-\overset{|}{NH}$$

wherein the upwardly directed bonds are connected to the R polymer molecule and the downwardly directed bonds are connected to δ groups; R₂ and R₃, identical or different, are hydrogen, alkyl, aryl or aralkyl; and
n is zero or an integer of 1 to 15.

2. A polymer in accordance with claim 1 wherein said $$-\delta-\underset{\gamma\quad\beta}{\underset{}{\bigcirc}}-\alpha$$

portion of said compound comprises 8-hydroxyquinoline, 2-formylphenol, 2-acetylphenol, 2-acylphenol or the oxime of 2-formylphenol, 2-acetylphenol or 2-acylphenol.

3. A polymer according to claim 1, wherein R is polystyrene or divinylbenzene cross-linked polystyrene.

4. A polymer according to claim 1, wherein R is polyacrylamide.

5. A polymer in accordance with claim 3, wherein R comprises macroporous styrene-divinylbenzene copolymer.

6. A polymer in accordance with one of claims 1 or 3 or 5, wherein X is —NH— and ε is —CH₂—.

7. A polymer in accordance with one of claims 1 or 3, wherein -X-ε- is $$\overset{|}{CH_2}-\overset{}{N}-(CH_2-CH_2-\overset{}{N})_n-CH_2-CH_2-\overset{|}{NH}$$

wherein the upwardly directed bonds are connected to the R polymer molecule and the downwardly directed bonds are connected to δ groups.

8. A polymer in accordance with claim 6, wherein said $$-\delta-\underset{\gamma\quad\beta}{\underset{}{\bigcirc}}-\alpha$$

portion of said polymer comprises 8-hydroxyquinoline, 2-formylphenol, 2-acetylphenol, 2-acylphenol or the oxime of 2-formylphenol, 2-acetylphenol or 2-acylphenol.

9. A polymer in accordance with claim 2, wherein R is polystyrene or divinylbenzene cross-linked styrene and -X-ε- is $$\overset{|}{CH_2}-\overset{}{N}-(CH_2-CH_2-\overset{}{N})_n-CH_2-CH_2-\overset{|}{NH}$$

wherein the upwardly directed bonds are connected to the R polymer molecule and the downwardly directed bonds are connected to δ groups.

10. A polymer in accordance with claim 2, wherein R is a polystyrene of divinylbenzene cross-linked styrene, ε is —CH₂—(OCH₂—CH₂)ₙ—, and X is —O—.

* * * * *